United States Patent [19]
Arnaud et al.

[11] Patent Number: 5,961,998
[45] Date of Patent: *Oct. 5, 1999

[54] GLOSSY COMPOSITION CONTAINING AROMATIC OILS THICKENED BY A POLYSACCHARIDE ETHER

[75] Inventors: Pascal Arnaud, L'Hay les Roses, France; Carlos Pinzon, New Milford, N.J.

[73] Assignee: L'Oreal, Paris, France

[ * ] Notice: This patent is subject to a terminal disclaimer.

[21] Appl. No.: 09/112,002

[22] Filed: Jul. 8, 1998

[30] Foreign Application Priority Data

Jul. 8, 1997 [FR] France .................................. 97 08675

[51] Int. Cl.$^6$ .............................. A61K 6/00; A61K 7/00; A61K 7/025
[52] U.S. Cl. ............................................. 424/401; 424/64
[58] Field of Search ........................................ 424/64, 401

[56] References Cited

U.S. PATENT DOCUMENTS 5,738,841 4/1998 Mellul et al. .............................. 424/59
5,849,275 12/1998 Calello et al. ............................. 424/64

FOREIGN PATENT DOCUMENTS 0 281 360  7/1988  European Pat. Off. .

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

A composition comprising (1) a liquid fatty phase comprising at least one aromatic group-containing oil other than benzene or toluene, (2) a particulate phase, and (3) a thickening agent for the fatty phase, wherein the thickening agent includes at least one polysaccharide ether, and wherein the polysaccharide structure comprises at least two different monosaccharide units, and each unit comprises at least one hydroxyl group etherified by a saturated or unsaturated hydrocarbon chain, and cosmetic use of the composition on the skin and/or lips to limit migration of makeup and care products containing the compositions.

30 Claims, No Drawings

GLOSSY COMPOSITION CONTAINING AROMATIC OILS THICKENED BY A POLYSACCHARIDE ETHER

BACKGROUND OF THE INVENTION

1. Field of the Invention

The present invention relates to a glossy composition containing aromatic oils thickened with a novel thickener, this composition being intended in particular for the cosmetics and/or dermatological fields. More especially, the invention relates to a make-up composition for the skin and/or mucous membranes such as the lips and the inside of the lower eyelids of human beings. The invention also relates to a use of this composition and to a cosmetic process to treat, make up and/ or care for the skin and/or mucous membranes. This composition can be in the form of a stick or dish, a soft paste or alternatively a relatively thickened oily liquid. It constitutes in particular a lip product, a foundation, an eye liner, a concealer product, an eye shadow or an antisun product.

2. Description of the Related Art

In cosmetic or dermatological products, it is common to find a thickened liquid fatty phase; this is particularly the case in anhydrous exfoliants, care gels or ointments, solid compositions such as deodorants, balms and lipsticks. Thickening of the oils (or of the phases which are liquid at room temperature) makes it possible in particular to limit the exudation of the oils from the solid compositions and, in addition, in the case of lipsticks, to limit or even totally prevent the migration of the coloured film in the wrinkles and fine lines around the lips. This problem of migration also exists, to a lesser extent, in the products used around the eyes.

To overcome these problems, use has usually been made of waxes or fillers. However, these waxes and fillers have a tendency to make the composition matt, which is not always desirable, since women are increasingly seeking a glossy lipstick which does not exude and does not migrate.

One of the known techniques for increasing the gloss of a make-up or care product is to increase the proportion of the oily phase at the expense of the particulate phase, the latter moreover needing to be as dispersed as possible, since poor dispersion of the pigmentary particles can lead to a non-uniform film on the lips, giving a relatively unaesthetic appearance. Furthermore, too low an amount of pigments often leads to a film which does not cover well. In addition, the composition's gloss has a tendency to decrease over time, in particular on account of the poor staying power of the film over time.

It is moreover known to thicken oils (or, in general, fatty phases which are liquid at room temperature) with polymeric thickeners and in particular polyolefins. Unfortunately, these known oil thickeners must be used in large amount in order to obtain effective thickening. However, too large an amount of thickener gives the composition, when it is intended for the cosmetics field, insufficient cosmetic properties, and in particular a sticky feel and a lack of slipperiness, these drawbacks potentially being very annoying, or even offputting.

It has been discovered, surprisingly and unexpectedly, that it is possible to obtain glossy and stable cosmetic compositions in the form of a gel, stick or supple paste having satisfactory cosmetic properties, by means of a specific liquid fatty phase thickened with a specific thickener. This composition makes it possible in particular to solve the drawbacks mentioned above.

SUMMARY OF THE INVENTION

The object of the present invention is thus a composition containing a liquid fatty phase containing at least one oil having a chemical structure containing at least one aromatic group, a thickener for the said fatty phase and a particulate filler, this thickener comprising at least one polysaccharide ether formed of units containing at least two different saccharide rings, each unit containing at least one hydroxyl group etherified by a saturated or non-saturated hydrocarbon-based alkyl chain.

By virtue of this specific thickener and this choice of fatty phase, the composition according to the invention makes it possible to obtain a glossy film on the skin or the lips. It is also possible to obtain, in combination with ingredients known to rigidify or solidify the composition, a solid product in the form of a supple paste or a stick which has improved cosmetic properties when compared with the thickened compositions of the prior art. In particular, it is possible to obtain a tube of lipstick, a concealer stick or a cast foundation, which is soft to apply, has a glossy appearance and in which the liquid fatty phase does not exude. Furthermore, in the more specific case of a lipstick, the pigment-filled oils do not migrate in the wrinkles and fine lines in the comers of the lips.

Although the invention is particularly suitable for the cosmetics field, it applies to any field which requires the production of glossy thickened compositions or even glossy solid compositions, and in particular in the veterinary, dermatological and pharmaceutical sectors, or alternatively in the wood sector (stick of pigments, oils and waxes for furniture restoration).

DETAILED DESCRIPTION OF THE INVENTION

In the thickener of the invention, the expression "hydrocarbon-based alkyl chain" is understood to refer to a linear or branched chain containing from 1 to 24, preferably from 1 to 10, better still from 1 to 6 and more especially from 1 to 3, carbon atoms. In particular, the alkyl chain is chosen from saturated chains and in particular methyl, ethyl, ethenyl, n-propyl, propenyl, isopropyl, n-butyl, isobutyl, tert-butyl and n-pentyl. These alkyl ethers can be manufactured as described in the documents EP-A-708,114 and EP-A-281,360.

According to a preferred embodiment of the invention, the polysaccharide ether has a weight-average molecular weight of greater than 100,000, and preferably greater than 200,000. This average molecular weight can range up to 1 million. This alkyl ether can contain from one to six, and preferably from two to four, hydroxyl groups per unit, etherified by a saturated or unsaturated hydrocarbon-based alkyl chain.

The saccharide rings are chosen in particular from mannose, galactose, glucose, furanose, rhamnose and arabinose.

According to a preferred embodiment of the invention, the polysaccharide ether is an alkyl ether of a gum and more particularly of a gum which is nonionic overall, i.e. one which contains few or no ionic groups. As appropriate gums, mention may be made, for example, of guar gum, in which the unit comprises a galactose and a mannose, carob gum, in which the unit comprises a galactose and a mannose, karaya gum, which is a complex mixture of rhamnose, galactose and galacturonic acid, and gum tragacanth, which is a complex mixture of arabinose, galactose and galacturonic acid.

According to a preferred embodiment of the invention, the polysaccharide ether is a guar gum derivative. Thus, advantageously, the alkyl ether is an alkylated galactomannan with a $C_1$ to $C_6$ and better still $C_1$ to $C_3$ alkyl chain, and more particularly ethylated guar having a degree of substitution of 2 to 3 and in particular of about 2.5 to 2.8, as described in the documents RD 95378007 (October 1995) and EP-A-708,114. This gum is, in particular, the one sold by the company Aqualon under the name N-HANCE-AG 200™ and N-HANCE-AG 50™.

The alkyl ether concentration depends on the desired pharmaceutical form and the desired consistency of the composition, as well as on the amount of oil to be thickened. In particular, the weight ratio of the amount of liquid fatty phase to the amount of thickener is chosen, for example, in the range from 5 to 500. The composition according to the invention can contain, for example, an amount of polysaccharide ether ranging from 0.2 to 16% of the total weight of the composition, preferably from 0.5 to 16% and better still from 1.5 to 8%.

The composition of the invention contains one or more oils containing an aromatic group. These oils can have a hydrocarbon-based or silicone-based skeleton optionally with fluoro groups. The chemical structure of these oils can contain one or more aryl or aralkyl radicals which can be mono- or multisubstituted. These aryl or aralkyl radicals can have from 6 to 60 carbon atoms.

According to the invention, the oils with a hydrocarbon-based skeleton and an aromatic group contain at least 8 carbon atoms and are not solvents of the benzene or toluene type.

As examples of oils containing a hydrocarbon-based skeleton with a monosubstituted aryl radical, mention may be made of benzoic acid esters such as ethyl hexyl benzoate, ($C_{12}$–$C_{15}$) alkyl benzoate, octyldodecyl benzoate and dipropylene glycol dibenzoate, and mixtures thereof.

As examples of oils containing a hydrocarbon-based skeleton with a multisubstituted aryl radical, mention may be made of trimellitic acid esters (or trialkyl trimellitates) with $C_1$ to $C_{22}$ alkyl chains, such as tridecyl trimellitate; para-methoxycinnamic acid esters, such as ethylhexyl para-methoxycinnamate and 2-ethoxyethyl para-methoxycinnamate; dimethyl-para-aminobenzoic acid esters, such as octyldimethyl PABA (or 2-ethylhexyl dimethyl-para-aminobenzoate); salicylic acid esters, such as 2-ethylhexyl salicylate; anthranilic acid esters, such as menthyl anthranilate; and mixtures thereof.

As examples of oils containing a silicone-based skeleton with one or more monosubstituted aryl radicals, mention may be made of the phenylsilicones especially having the following formula:

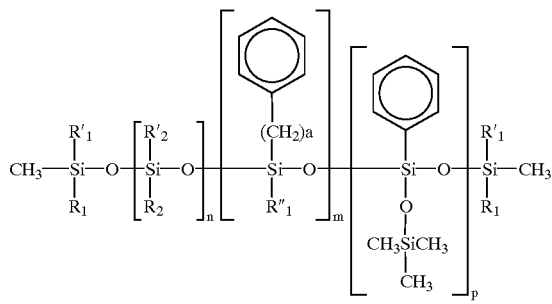

in which $R_1$, $R'_1$ and $R''_1$ represent independently a $C_1$ to $C_{30}$ linear or branched, saturated or unsaturated alkyl radical, an aryl radical, a phenyl radical or a $C_7$ to $C_{60}$ aralkyl radical, $R_2$ and $R'_2$ represent independently a $C_1$ to $C_{30}$ linear or branched, saturated or unsaturated alkyl radical, n is an integer ranging from 0 to 150, m is an integer ranging from 0 to 200, p is an integer ranging from 0 to 200, and a is an integer ranging from 0 to 10, with the proviso that the ratio n/(n+m+p) is at most equal to 0.85 and that the sum n+m+p ranges from 1 to 200, and with the further proviso that if m=p=0, then $R'_1$ is an aryl or aralkyl radical.

Preferably, $R_1$ and $R'_1$ are equal and represent a methyl, ethyl, propyl, isopropyl, decyl, dodecyl or octadecyl radical or alternatively a phenyl, tolyl, benzyl or phenethyl radical.

Advantageously, $R_2$ and $R'_2$ are equal and represent a methyl, ethyl, propyl, isopropyl, decyl, dodecyl or octadecyl radical, and better still methyl.

Preferably, $R''_1$ is a methyl, ethyl, propyl, isopropyl, decyl, dodecyl or octadecyl radical, or alternatively a phenyl, tolyl, benzyl or phenethyl radical. In particular, it is equal to methyl or phenyl.

Among these phenylsilicones, mention may be made in particular of phenyltrimethicones, phenyltrimethylsiloxydiphenylsiloxanes, diphenylmethyldiphenyltrisiloxanes, 2-phenylethyltrimethylsiloxysilicates, diphenylmethyldimethyltrisiloxanes, diphenyldimethicones, phenyldimethicones, polymethylphenylsiloxanes, phenyltrimethicones and mixtures thereof. As examples of commercial phenylsilicones, mention may be made of the oil Belsil PDM 1000 sold by the company Wacker, the oils DC556, SF558 or DC704 sold by the company Dow Corning, the oil Abil AV8853 from Goldschmidt, the oil Silbione 70641V200 or the oil Silbione 70633V30 sold by the company Rhône-Poulenc, or alternatively those sold by the company PCR under the names 15M30, 15M40, 15M50 and 15M60.

As other silicone oils with an aromatic group which can be used in the invention, mention may be made of resins modified with styryl groups, such as those described in U.S. Pat. No. 5,338,538 and U.S. Pat. No. 5,397,566 from General Electric, and in particular the phenyl ethyl trimethylsiloxysilicates, such as those sold under the name 1170–3100. It is also possible to use fluorosilicone oils containing an aromatic group, and in particular perfluoro, such as he ones described in documents EP-A-811,369 and EP-A-829,254; the perfluoro radicals are pendent radicals having from 1 to 12 carbon atoms.

The composition according to the invention comprises from 1 to 99.8% by weight, preferably from 5 to 80%, of oils containing an aromatic group.

The particulate phase of the composition of the invention is generally present in a proportion of from 0.05 to 35% of the total weight of the composition, preferably from 0.5 to 20%, and which can comprise pigments and/or pearlescent agents and/or fillers usually used in cosmetic or dermatological compositions. This filler can lead to a coloured, white or colourless composition.

The term "pigments" should be understood to mean white or coloured, inorganic or organic particles, which are insoluble in the liquid fatty phase and which are intended to colour and/or opacify the composition.

The term "fillers" should be understood to mean colourless or white, inorganic or synthetic, lamellar or non-lamellar particles.

The term "pearlescent agents" should be understood to mean iridescent particles produced in particular by certain molluscs in their shells, or alternatively synthesized. These fillers and pearlescent agents serve in particular to modify the texture of the composition.

The pigments can be present in the composition in a proportion of from 0.05 to 25% of the weight of the final composition, and preferably in a proportion of from 2 to 15%. As inorganic pigments which can be used in the invention, mention may be made of titanium, zirconium or cerium oxide, as well as zinc, iron or chromium oxide and ferric blue. Among the organic pigments which can be used in the invention, mention may be made of carbon black and barium, strontium, calcium (DC Red No. 7) and aluminium lakes.

The pearlescent agents can be present in the composition in a proportion of from 0 to 20% of the total weight of the composition, preferably at a high level of about 1 to 15%. Among the pearlescent agents which can be used in the invention, mention may be made of mica coated with titanium oxide, with iron oxide, with natural pigment or with bismuth oxychloride, such as coloured titanium mica.

The fillers can be present in a proportion of from 0 to 35% of the total weight of the composition, preferably 0.5 to 15%. Mention may be made in particular of talc, mica, kaolin, Nylon powders (Orgasol in particular) and polyethylene powder, Teflon, starch, boron nitride, copolymer microspheres such as Expancel (Nobel Industrie), Polytrap (Dow Corning) and microbeads of silicone resin (Tospearl from Toshiba, for example).

Advantageously, the liquid fatty phase contains one or more types of oil other than the oils containing an aromatic group. These oils can be hydrocarbon-based and/or silicone-based and/or fluoro oils. These oils can be of animal, plant, mineral or synthetic origin.

As oils other than those containing an aromatic group, which can be used in the invention, mention may be made in particular of:

- hydrocarbon-based oils of animal origin, such as perhydrosqualene;
- hydrocarbon-based plant oils, such as liquid triglycerides of fatty acids of 4 to 10 carbon atoms, such as heptanoic or octanoic acid triglycerides, or alternatively sunflower oil, corn oil, soybean oil, marrow oil, grapeseed oil, sesame oil, hazelnut oil, apricot oil, macadamia oil, castor oil, avocado oil, caprylic/capric acid triglycerides such as those sold by the company Stearineries Dubois or those sold under the names Miglyol 810, 812 and 818 by the company Dynamit Nobel, jojoba oil and karite butter;
- linear or branched hydrocarbons of mineral or synthetic origin, such as liquid paraffins and derivatives thereof, petroleum jelly, polydecenes, purcellin oil, and hydrogenated polyisobutene such as parleam;
- synthetic esters and ethers, in particular of fatty acids, such as the oils of formula $R_3COOR_4$ in which $R_3$ represents a higher fatty acid residue containing from 7 to 29 carbon atoms and $R_4$ represents a hydrocarbon-based chain containing from 3 to 30 carbon atoms, such as, for example, purcellin oil, isopropyl myristate, 2-ethylhexyl palmitate, 2-octyldodecyl stearate, 2-octyldodecyl erucate, isostearyl isostearate; hydroxylated esters, such as isostearyl lactate, octyl hydroxystearate, octyldodecyl hydroxystearate, diisostearyl malate, triisocetyl citrate, fatty alcohol heptanoates, octanoates and decanoates; polyol esters such as propylene glycol dioctanoate, neopentyl glycol diheptanoate and diethylene glycol diisononanoate; and pentaerythritol esters;
- fatty alcohols having from 12 to 26 carbon atoms, such as octyldodecanol, 2-butyloctanol, 2-hexyldodecanol, 2-undecylpentadecanol, oleyl alcohol;
- partially hydrocarbon-based and/or silicone-based fluoro oils, such as the one described in document JP-A-2, 295,912;
- silicone oils such as volatile or non-volatile, linear or cyclic polydimethylsiloxanes (PDMSs) which are liquid or pasty at room temperature;
- mixtures thereof.

These oils can represent from 0 to 99% by weight relative to the liquid fatty phase.

As volatile silicone oils which can be used in the invention, mention may be made of linear or cyclic silicones having from 2 to 7 silicon atoms, these silicones optionally containing alkyl groups having from 1 to 10 carbon atoms. Thus, these silicones are, in particular, hexamethyldisiloxane, cyclopenta- or cyclotetra- or cyclohexadimethylsiloxane. These volatile oils can represent from 0 to 50% of the total weight of the composition.

The composition according to the invention can in addition comprise any ingredient conventionally used in the fields considered, and more especially in the cosmetics and dermatological fields. These ingredients are chosen in particular from preserving agents, aqueous-phase or fatty-phase thickeners other than that of the invention, fragrances, surfactants, antioxidants, waxes and mixtures thereof. The composition according to the invention can also contain lipid vesicles of ionic and/or nonionic type. The amounts of these various ingredients are those used conventionally in the fields considered, and, for example, from 0.01% to 20% of the total weight of the composition. The nature of these ingredients and their proportion must be compatible with the production of stable, thickened and glossy compositions according to the invention. The composition can also contain water at a concentration ranging from 0 to 95% of the total weight of the composition.

The composition of the invention can advantageously comprise a solid or pasty fatty phase containing one or more gums and/or one or more waxes. These gums or waxes can be hydrocarbon-based, fluoro and/or silicone-based and can be of plant, mineral, animal and/or synthetic origin. In particular, the waxes have a melting point above 25° C. and better still above 45° C.

As waxes which can be used in the composition of the invention, mention may be made of lanolin, beeswax, carnauba wax, candelilla wax, paraffin, lignite wax, microcrystalline wax, ceresine or ozokerite; synthetic waxes such as polyethylene waxes, silicone waxes such as alkyl- or alkoxydimethicones having from 16 to 45 carbon atoms.

The nature and the amount of these gums or waxes depend on the desired mechanical properties and the desired textures. As a guide, the composition can contain from 0 to 50% by weight of waxes relative to the total weight of the composition, and better still from 5 to 30%.

The composition of the invention can be in any pharmaceutical form normally used for topical application, and in particular in the form of an oily gel, an oil-in-water or water-in-oil emulsion, or a dispersion of oil in water by means of vesicles, these vesicles being at the oil/water interface. This composition can have the appearance of a cream, a salve, a supple paste, an ointment, a cast or moulded solid and in particular a stick or a dish.

The composition according to the invention can advantageously be used to treat, make up or care for the skin and/or mucous membranes depending on the nature of the active agents used. In particular, the composition of the invention can be a tube of lipstick, a lip gloss, which can be used as it is or applied to a film of lipstick, in particular in order to increase its gloss and/or to reduce the migration of the oils (top coat). It can also contain a solid foundation, a concealer product or a product for use around the contours of the eyes, an eyeliner, a mascara or an eyeshadow, or alternatively an antisun product or a skincare or skin cleansing product such as exfoliant products. These compositions can also contain cosmetic or dermatological active agents in order, in particular, to give the composition a caring or treating aspect. Thus, the composition can contain vitamins and other lipophilic active agents (lanolin, UVA screening agent) or hydrophilic active agents (moisturizers such as glycerol).

Thus, another object of the invention is a cosmetic use of the above composition to care for and/or make up the skin and/or mucous membranes and more especially the lips, as well as a use of this composition for the preparation of an ointment intended to treat the skin and/or mucous membranes and in particular the lips. The object of the invention is also a cosmetic and/or dermatological treatment process for the skin and/or mucous membranes and in particular the lips, this process consisting in applying the composition defined above to the skin and/ or mucous membranes and in particular the lips.

More specifically, the object of the invention is a lip product or foundation product containing a liquid fatty phase containing at least one oil having a chemical structure containing at least one aromatic group, a thickener for the said fatty phase and a particulate filler, this thickener comprising at least one polysaccharide ether as defined above.

The composition of the invention can be obtained by heating the various constituents to the temperature of the waxes with the highest melting points, followed by casting the molten mixture in a mould (dish or glove finger). It can also be obtained by extrusion as described in application EP-A-667,146.

The object of the invention is also the use, in a composition containing a liquid fatty phase and a particulate filler, of a combination of at least one oil having a chemical structure containing at least one aromatic group, and of a thickener for the said fatty phase, this thickener comprising at least one polysaccharide ether as described above, in order to reduce the migration of this liquid fatty phase and/or to obtain a glossy film.

The object of the invention is also a process for limiting the migration of a make-up or care composition for the skin or the lips on a substrate other than the said skin and the said lips, containing a liquid fatty phase and a particulate filler, this process consisting in introducing into the liquid fatty phase at least one oil having a chemical structure containing at least one aromatic group, this fatty phase being thickened with a thickener comprising at least one polysaccharide ether as defined above.

Having generally described this invention, a further understanding can be obtained by reference to certain specific examples which are provided herein for purposes of illustration only and are not intended to be limiting unless otherwise specified. The quantities are given therein in % by weight.

EXAMPLE 1

Lip Gloss

| Ethylated guar having a degree of substitution of about 2.5 | 3.8% |
|---|---|
| DC Red No. 7 calcium (lake) | 5.0% |
| Phenyltrimethicone (DC 556) | qs 100% |

This lip gloss is obtained by dispersing the pigments in the liquid fatty phase using a three-cylinder mill. The ethylated guar is then added and dissolved at 90° C. for 3 hours in the mixture. This mixture is then cooled to room temperature. The gel obtained can be applied to the lips with a lipstick brush. It gives a glossy lipstick coloration, the coloration and gloss being long-lasting.

This lip gloss was tested in comparison with a gloss of the prior art. It was judged to be more cosmetic and to have better staying power and gloss than the lip gloss of the prior art.

Examples 2 to 6

Lip gloss

These examples differ from that of Example 1 in the nature of the phenylated oil. These examples contain, respectively, phenyltrimethylsiloxydiphenylsiloxane (SF558); diphenyldimethicone (Silbione 70641V200); diphenylmethyldimethyltrisiloxane (DC704); 2-phenyl ethyl trimethylsiloxysilicate (1170–3100); tridecyl trimellitate (DUB TMTD).

Example 7

Lip gloss

| Ethylated guar having a degree of substitution of about 2.5 | 1.9% |
|---|---|
| DC Red No. 7 calcium (lake) | 5.0% |
| Phenyltrimethicone (Belsil PDM 1000) | qs 100% |

This composition can be used as it is as a lip gloss or as a top coat.

Example 8

Lipstick

| Ethylated guar having a degree of substitution of 2.5 | 4.00% |
|---|---|
| Polyethylene (wax) | 3.50% |
| Tridecyl trimellitate | 81.00% |
| Carnauba wax | 3.50% |
| DC Red 7 calcium (lake) | 8.00% |

The pigments are dispersed in the oil and the ethylated guar is then dissolved at 90° C. for 3 hours. The waxes are added and the mixture is heated until the waxes have completely melted. Finally, the mixture obtained is cast in a mould of suitable shape in order to obtain a tube.

Examples 9 and 10

Lipsticks

These examples differ from that of Example 9 by the use of a methylated guar and a propylated guar with a degree of substitution of about 2.7.

The disclosure of France priority patent application 97 08675, filed Jul. 8, 1997, is hereby incorporated herein by reference.

Obviously, numerous modifications and variations of the present invention are possible in light of the above teachings. It is therefore to be understood that within the scope of the appended claims, the invention may be practiced otherwise than as specifically described herein.

We claim:

1. A composition comprising (1) a liquid fatty phase comprising at least one aromatic group-containing oil other than benzene or toluene, (2) a particulate phase, and (3) a thickening agent for the fatty phase, wherein said thickening agent includes at least one polysaccharide ether, and wherein the polysaccharide structure comprises at least two different monosaccharide units, and each unit comprises at least one hydroxyl group etherified by a saturated or unsaturated hydrocarbon chain.

2. The composition according to claim 1, wherein each unit comprises two to four hydroxy groups etherified by a saturated or unsaturated hydrocarbon chain.

3. The composition according to claim 1, wherein the hydrocarbon chain has from 1 to 24 carbon atoms.

4. The composition according to claim 3, wherein the hydrocarbon chain has from 2 to 10 carbon atoms.

5. The composition according to claim 1, wherein the hydrocarbon chain is selected from the group consisting of methyl, ethyl, n-propyl, isopropyl, n-butyl, isobutyl, and tertbutyl.

6. The composition according to claim 1, wherein the monosaccharide units are selected from the group consisting of mannose, galactose, glucose, furanose, rhamnose, and arabinose.

7. The composition according to claim 1, wherein the polysaccharide ether is an ether of a gum selected from the group consisting of guar gum, carob gum, karaya gum, tragacanth gum and mixtures thereof.

8. The composition according to claim 1, wherein the polysaccharide ether is a $C_1$ to $C_6$-alkylated galactomannan.

9. The composition according to claim 1, wherein the polysaccharide ether is an ethylated guar gum with a degree of substitution of 2 to 3.

10. The composition according to claim 1, wherein the polysaccharide ether has a molecular weight in excess of 200,000.

11. The composition according to claim 1, wherein the weight ratio of liquid fatty phase to thickening agent is from about 5:1 to about 500:1.

12. The composition according to claim 1, wherein the polysaccharide ether is present in an amount of from about 0.2 to about 16% of the total weight of the composition.

13. The composition according to claim 12, wherein the polysaccharide ether is present in an amount of from 1.5 to 8% of the total weight of the composition.

14. The composition according to claim 1, wherein the aromatic group-containing oil contains at least one aryl or aralkyl radical having 6 to 60 carbon atoms.

15. The composition according to claim 1, wherein the aromatic group-containing oil is a silicone oil with the formula:

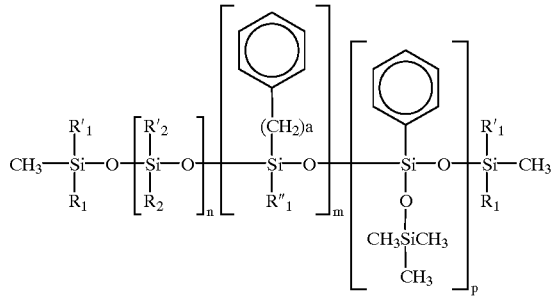

in which $R_1$, $R'_1$ and $R''_1$ represent independently a $C_1$ to $C_{30}$ linear or branched, saturated or unsaturated alkyl radical, an aryl radical, a phenyl radical or a $C_7$ to $C_{60}$ aralkyl radical, $R_2$ and $R'_2$ represent independently a $C_1$ to $C_{30}$ linear or branched, saturated or unsaturated alkyl radical, n is a whole number going from 0 to 150, m is a whole number going from 0 to 200, p is a whole number going from 0 to 200, and a is a whole number going from 0 to 10, with the proviso that the ratio n/(n+m+p) is at most equal to 0.85 and that the sum n+m+p goes from 1 to 200 and with the further proviso that if m=p=0, then $R'_1$ is an aryl or aralkyl radical.

16. The composition according to claim 15, wherein each of $R_1$, $R'_1$ and $R''_1$ is selected from the group consisting of methyl, ethyl, propyl, isopropyl, decyl, dodecyl, octadecyl, phenyl, tolyl, benzyl, and phenethyl.

17. The composition according to claim 16, wherein each of $R_2$ and $R'_2$ is selected from the group consisting of methyl, ethyl, propyl, isopropyl, decyl, dodecyl, and octadecyl.

18. The composition according to claim 1, wherein the aromatic group-containing oil is selected from the group consisting of $C_1$ to $C_{22}$ alkyl esters of trimellitic acid, esters of benzoic acid, esters of dimethyl para-methoxycinnamic acid, esters of paraamino benzoic acid, esters of salicylic acid, esters of anthranilic acid, phenyl trimethicones, phenyltrimethylsiloxydiphenylsiloxanes, diphenylmethyl dimethyltrisiloxanes, diphenyl dimethicones, phenyl ethyl trimethylsiloxysilicates, phenyltrimethicones and polymethylphenyisiloxanes, and mixtures thereof.

19. The composition according to claim 1, wherein the aromatic group-containing oil is selected from the group consisting of tridecyl trimellitate, para-methoxycinnamate, phenyl trimethicones, phenyltrimethylsiloxydiphenylsiloxanes, diphenyl dimethicones, diphenylmethyldiphenyl trisiloxanes, 2-phenylethyl trimethylsiloxysilicates, and mixtures thereof.

20. The composition according to claim 1, wherein the fatty phase contains at least one oil other than the aromatic group-containing oil selected from the group consisting of oils of animal, vegetable, mineral or synthetic origin.

21. The composition according to claim 1, wherein the particulate phase is present in an amount of about 0.05 to about 35% of the total weight of the composition.

22. The composition according to claim 1, which is in the form of an oily gel, a water-in-oil or oil-in-water emulsion or a dispersion of oil in water with the aid of vesicles.

23. The composition according to claim 1, which additionally contains at least one ingredient selected from the group consisting of fragrances, preservatives, waxes, lipophilic active components.

24. The composition according to claim 1, which is in the form of a lipstick, lip balm, lip gloss or top coat.

25. The composition according to claim 8, wherein the polysaccharide ether is a $C_1$ to $C_3$-alkylated galactomannan.

26. The composition according to claim 21, wherein the particulate phase is present in an amount of 0.5 to 20% of the total weight of the composition.

27. The composition according to claim 1, wherein the aromatic group-containing oil has at least 8 carbon atoms.

28. An ointment intended for treating the lips comprising the composition of claim 1.

29. A process for cosmetic treatment of the lips, comprising applying to the lips the composition of claim 1.

30. A process for limiting the migration of a composition for makeup or care of the skin or the lips from said skin or said lips, said composition containing a liquid fatty phase and a particulate filler, comprising introducing into said liquid fatty phase at least one aromatic group-containing oil having at least 8 carbon atoms, and a thickening agent which includes at least one polysaccharide ether, wherein the polysaccharide structure comprises at least two different monosaccharide units, and each unit comprises at least one hydroxyl group etherified by a saturated or unsaturated hydrocarbon chain.

* * * * *